United States Patent [19]

Lappi et al.

[11] Patent Number: 5,191,067
[45] Date of Patent: Mar. 2, 1993

[54] FIBROBLAST GROWTH FACTOR CONJUGATES

[75] Inventors: Douglas A. Lappi, Del Mar; Andrew Baird, San Diego, both of Calif.

[73] Assignee: The Salk Institute for Biological Studies, San Diego, Calif.

[21] Appl. No.: 344,109

[22] Filed: Apr. 27, 1989

[51] Int. Cl.$^5$ .................. C07K 7/00; C07K 13/00; A61K 37/36
[52] U.S. Cl. .................. 530/399; 514/2; 514/12; 514/21; 530/300; 530/324; 530/350; 530/402
[58] Field of Search ............... 530/399, 402, 350, 300, 530/324, 345; 514/2, 21, 12

[56] References Cited

U.S. PATENT DOCUMENTS 5,116,753  5/1992  Beattie et al. .............. 435/240.2

FOREIGN PATENT DOCUMENTS 0259904  3/1988  European Pat. Off. .

OTHER PUBLICATIONS

Grindey, Cancer Cells, vol. 2, No. 6, pp. 163-171 (1990).
Siegall et al., FASEB Journal, vol. 5 pp. 2843-2849 (1991).
Biro et al., New York Acad. Sci. Abstracts, p. 16, Jan. 16-18, 1991.
Taetle et al. J. Nat. Cancer Inst. vol. 50 (13) pp. 1053-1059 Sep. 1988.
J. Folkman et al., "Angiogenic Factors" Science 235:442-447 (1987).
D. Lappi et al., "Biological and Chemical Characterization of Basic EGF-Saporin Mitotoxin" Biochem. Biophys. Res. Commun. 160:917-923 (1989).
Baird et al., Molecular Characterization of Fibroblast Growth Factor: Distribution and Biological Activities in Various Tissues, Recent Progress in Hormone Res. 42:143-205 (1986).
Esch et al., Primary structure of bovine pituitary basic fibroblast growth factor (FGF) and comparison with the amino-terminal sequence of bovine brain acidic FGF Proc. Natl. Acad. Sci. USA, 82:6507-6511 (1985).
Esch et al., Primary Structure of Bovine Brain Acidic Fibroblast Growth Factor (FGF), Biochemical and Biophysical Research Communications 133:554-562 (1985).
Baird et al., Receptor- and heparin-binding domains of basic fibroblast growth factor, Proc. Natl. Acad. Sci. USA 85:2324-2328 (1988).
Patricia Walicke and Andrew Baird, Neurotrophic effects of basic and acidic fibroblast growth factors are not mediated through glial cells, Developmental Brain Research 40:71-79 (1988).
Cuevas et al., Basic Fibroblast Growth Factor (FGF) Promotes Cartilage Repair In Vivo, Biochem. and Biophys. Res. Comm. 156:611-618 (1988).
Halaban et al., bFGF as an Autocrine Growth Factor for Human Melanomas, Oncogene Research 3:177-186, (1988).

(List continued on next page.)

Primary Examiner—Jeffrey E. Russel
Assistant Examiner—Andrew G. Rozycki
Attorney, Agent, or Firm—Fitch, Even, Tabin & Flannery

[57] ABSTRACT

The invention provides a conjugate comprising FGF or other polypeptide reactive with an FGF receptor, and a cytotoxic agent. The cytotoxic agent can be a ribosome-inactivating protein (RIP), such as saporin, although other cytotoxic agents can also be advantageously used. The cytotoxic agent can be attached to FGF through a chemical bond or the composition can be prepared as a chimera, using techniques of recombinant DNA. The conjugate can be used to treat FGF-mediated pathophysiological conditions by specifically targeting cells having FGF receptors and inhibiting proliferation of or causing death of the cells. Additionally, the conjugate can be used to target cytotoxic agents into cells having FGF receptors, and to inhibit the proliferation of such cells. A method of purifying the conjugate on an immobilized heparin column is also provided.

2 Claims, 6 Drawing Sheets

OTHER PUBLICATIONS

Bregni et al., Activity of a Monoclonal Antibody-Saporin-6 Conjugate Against B-Lymphoma Cells, J. National Cancer Institute 80:511–517 (1988).

Siena et al., Synthesis and Characterization of an Antihuman T-Lymphocyte Saporin Immunotoxin (OKT-1-SAP) With in vivo Stability Into Nonhuman Promates, Blood 72:756–765 (1988).

Siena et al., Evaluation of Antihuman T Lymphocyte Saporin Immunotoxins Potentially Useful in Human Transplantation, Transplantation 46:747–753 (1988).

Bergamaschi et al., Killing of K562 cells with conjugates between human transferrin and a ribosome-inactivating protein (SO-6), British J. of Haematology 68:379–384 (1988).

Chaudhary et al., Activity of a recombinant fusion protein between transforming growth factor type alpha and Pseudomonas toxin, Proc. Natl. Acad. Sci. USA, 84:4538–4542 (Jul. 1987).

Case et al., Chimeric cytotoxin IL2–PE40 delays and mitigates adjuvant-induced arthritis in rats, Proc. Natl. Acad. Sci. USA 86:287–291 (1989).

FitzGerald et al., Adenovirus-Induced release of epidermal growth factor and pseudomonas into the cytosol of KB cells during receptor-mediated endocytosis, Cell 32:607–617 (1983).

Siegall et al., Cytotoxic activity of an interleukin 6-Pseudomonas exotoxin fusion protein on human myeloma cells, Proc. Natl. Acad. Sci. USA 85:9738–9742 (1988).

Lorberboum-Galski et al., Cytotoxic activity of an interleukin 2-Pseudomonas exotoxin chimeric protein produced in Escherichia coli Proc. Natl. Acad. Sci. USA 85:1922–1926.

Siegall et al., Cytotoxic activities of a fusion comprised of TGFalpha and Pseudomonas exotoxin, FASEB Journal 3:2647–2652 (1989).

Lorberboum-Galski et al., Cardiac allograft survival in mice treated with IL-2-PE40, Proc. Natl. Acad Sci. USA 86:1008–1012 (1989).

Akiyama et al., Verapamil enhances the toxicity of conjugates of epidermal growth factor with Pseudomonas Exotoxin and antitransferrin receptor with Pseudomonas Exotoxin, J. Cell. Phys. 120:271–279 (1984).

Vollmar et al., Toxicity of ligand and antibody-directed ricin A-chain conjugates recognizing the epidermal growth factor receptor, J. Cell. Phys. 131:418–425 (1987).

Bacha et al., Thyrotropin-releasing hormone-diptheria toxin-related polypeptide conjugates, J. Biol. Chem. 258:1565–1570 (1983).

Chaudhary et al., Selective killing of HIV-infected cells by recombinant human CD4-Pseudomonas exotoxin hybrid protein, Nature 355:369–372 (1988).

Bacha et al., Organ-specific binding of a thyrotropin-releasing hormone-diptheria toxin complex after intravenous administration to rats, Endocrinology 113:10721076 (1983).

Schwartz et al., A new cytotoxin specific for the target cells of corticotropin-releasing factor, Endocrinology 121:14541460 (1897).

Lorberboum-Galski et al., Interleukin 2 (IL2) PE40 is cytotoxic to cells dislaying either the p55 or p70 subunit of the IL2 receptor, J. Biol. Chem. 263:18650–18656 (1988).

Kelley et al., Interleukin 2-diptheria toxin fusion protein can abolish cell-mediated immunity in vivo, Proc. Natl. Acad. Sci. USA 85:3980–3984 (1988).

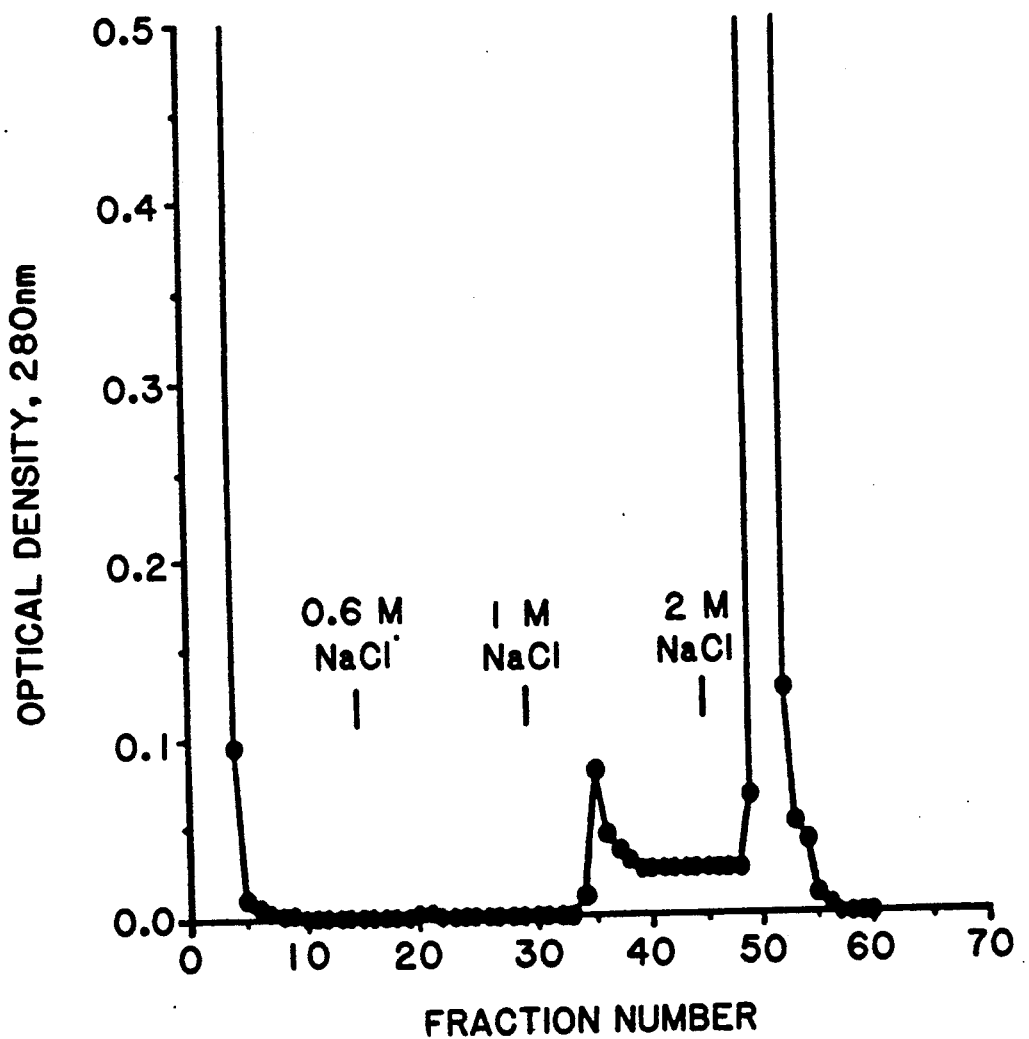

FIBROBLAST GROWTH FACTOR CONJUGATES

BACKGROUND OF THE INVENTION

This invention relates to compositions which inhibit cell proliferation, and, more specifically, to fibroblast growth factor conjugated to a cytotoxic agent.

A great deal of attention has been directed towards the identification and characterization of factors capable of stimulating the growth and proliferation of specific cell types. In the last twenty-five years, a number of such mitogenic factors have been isolated. Rather than having highly specific activities as may have been originally anticipated, many such growth factors are now recognized to have multifunctional activities, affecting a wide spectrum of cell types. In addition, certain activities are shared by homologous members of a family of growth factors.

One family of growth factors now known to have a broad spectrum of activities is the fibroblast growth factors (FGF). Basic FGF is a protein which has a molecular weight of approximately 16 kD, is acid and temperature sensitive and has a high isoelectric point. A structurally related protein, acidic FGF, has an acidic isoelectric point. FGFs exhibit a mitogenic effect on a wide variety of mesenchymal, endocrine and neural cells. Of particular interest is their stimulatory effect on collateral vascularization and angiogenesis. Such mitogenic effects have stimulated considerable interest in FGF as potential therapeutic agents for wound healing, nerve regeneration and cartilage repair, for example.

Cells that respond to basic FGF have been shown to possess specific receptors on the cell surface membranes. The receptor proteins appear to be single chain polypeptides with molecular weights ranging from 110 to 150 kD, depending on cell type. The proteins bind basic FGF with high affinity ($Kd = 10$–$80$ pM), with receptor numbers ranging from 2000 to 80,000 per cell. The receptors can be purified from rat brain, using a combination of lectin and ligand affinity chromatography and are associated with tyrosine kinase activity (Imamura et al., Biochem. Biophys. Res. Comm. 155:583–590 (1988); Huang and Huang, J. Biol. Chem. 261:9568–9571 (1986), both of which are incorporated herein by reference).

On baby hamster kidney cells (BHK), two basic FGF receptors with estimated molecular weights of 110 and 130 kD have been reported (Neufeld and Gaspodarowicz, J. Biol. Chem. 260:13860–13868 (1985); Neufeld and Gaspodarowicz, J. Biol. Chem. 261:5631–5637 (1986), both of which are incorporated herein by reference). Both receptor proteins bind basic FGF and acidic FGF, although it appears that the larger binds basic FGF preferentially while the smaller has somewhat higher affinity for acidic FGF.

In addition to potentially useful proliferative effects, basic FGF induced mitogenic stimulation may, in some instances, be detrimental. For example, cell proliferation and angiogenesis are an integral aspect of tumor growth. Basic FGF is thought to play a pathophysiological role, for example, in tumor development, atherosclerosis, rheumatoid arthritis, proliferative diabetic retinopathies and other complications of diabetes.

There thus exists a need to inhibit detrimental mitogenic effects of basic FGF in certain pathological conditions. The present invention satisfies this need and provides related advantages as well.

SUMMARY OF THE INVENTION

The invention provides a conjugate comprising basic FGF or other polypeptide reactive with an FGF receptor, and a cytotoxic agent. In one embodiment, the cytotoxic agent is a ribosome-inactivating protein (RIP), such as, for example, saporin, although other cytotoxic agents can also be advantageously used. The cytotoxic agent can be attached to basic FGF through a chemical bond or the composition can be prepared as a chimera, using techniques of recombinant DNA. In both cases, the conjugate molecule is designed and produced in such a way that the receptor-binding epitope of the basic FGF moiety of the complex is left available for recognition by the FGF receptor.

The conjugate can be used to treat FGF-mediated pathophysiological conditions by specifically targeting to cells having FGF receptors and inhibiting proliferation of or causing death of the cells. Such pathophysiological conditions include, for example, tumor development, atherosclerosis, Dupuytren's Contracture, certain complications of diabetes such as proliferative diabetic retinopathies, and rheumatoid arthritis. The treatment is effected by administering a therapeutically effective amount of the FGF conjugate, for example, in a physiologically acceptable excipient. Additionally, the conjugate can be used to target cytotoxic agents into cells having FGF receptors, and to inhibit the proliferation of such cells. A method of purifying the conjugate on a heparin immobilized column is also provided.

BRIEF DESCRIPTION OF THE DRAWINGS

FIG. 1 shows a heparin Sepharose chromatography of the conjugation reaction mixture.

DETAILED DESCRIPTION OF THE INVENTION

Figure 2A:
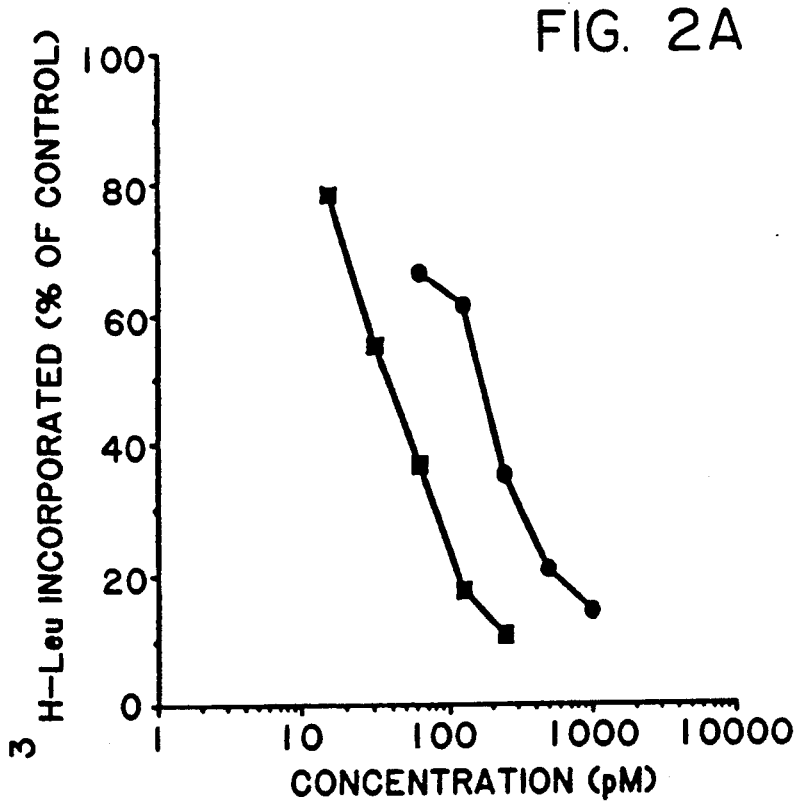
FIG. 2 shows the RIP and binding activities of the basic FGF/SAP conjugate. The activity was compared to SAP, alone in a cell-free protein synthesis inhibition assay (FIG. 2A) (SAP ■, basic FGF-SAP ●) and the receptor binding activity was compared to basic FGF in the BHK radioreceptor assay (FIG. 2B) (basic FGF □, basic FGF-SAP ●). Each point is the mean of 3 replicates. Standard deviations were less than 10%.

The present invention provides a conjugate comprising basic FGF or other polypeptide reactive with an FGF receptor and a cytotoxic agent, which composition is effective for inhibiting growth and proliferation of cells having FGF receptors. The composition can be used to counteract the mitogenic effects of basic FGF, where such an effect is deleterious, such as in tumor angiogenesis, atherosclerosis, and proliferative complications of diabetes such as proliferative retinopathies.

As used herein, the term "FGF" refers to both basic FGF (bFGF) and acidic FGF (aFGF) and other proteins exhibiting basic FGF mitogenic activity mediated through binding to an FGF receptor. For example, a basic FGF peptide having a molecular weight of about 16 kD, and a pI of about 9.6, has been described by Esch et al. Other FGF proteins include other forms of basic FGF which have an amino terminal extension, aFGF, hst, int-2 and FGF-5. (See Baird et al., Brit. Med. Bull 45:438–452 (1989)). All express mitogenic activity in a wide variety of normal diploid mesoderm-derived and neural crest-derived cells. A test of such "FGF mitogenic activity" is the ability to stimulate proliferation of cultured bovine aortic endothelial cells, as described in Gospodarowicz et al., J. Biol. Chem. 257:12266–12278 (1982); Gospodarowicz et al., Proc. Natl. Acad. Sci. USA 73:4120–4124 (1976), which are incorporated herein by reference. The term FGF refers both to proteins having amino acid sequences found in a mammalian host, as well as modified sequences, having amino acid substitutions, deletions, insertions or additions, which still express mitogenic activity, mediated through binding to an FGF receptor. Purified preparations of basic FGF and acidic FGF are frequently observed to include several molecular forms of the mitogens. It is understood that differences in amino acid sequences can occur in FGF from different species as well as between FGF from individual organisms of species. The term is intended to refer to both proteins isolated from natural sources as well as those made synthetically, as by chemical synthesis or recombinant means.

The amino acid sequence of an exemplary mammalian basic FGF derived from bovine pituitary tissue is provided in Esch et al., Proc. Natl. Acad, Sci. USA 82:6507–6511 (1985), which is incorporated herein by reference. As used herein, the term "basic FGF" refers to proteins or polypeptides having substantially the same amino acid sequence and mitogenic activity as that of the basic FGF described in Esch, supra. cDNAs encoding human aFGF (Jaye et al., Science 233:541–545 (1986) and bovine (Abraham et al., Science 233:545–548 (1986), human (Abraham et al., EMBO J. 5:2523–2528 (1986); Abraham et al., Quant. Biol. 51:657–668 (1986), and rat (Shimasaki et al., Biochem. Biophys. Res. Commun. 1988; Kurokawa et al., Nucleic Acids Res. 16:5201 (1988)) basic FGF have been cloned, and sequenced and predict the existence of proteins identical to those found by protein sequencing.

As used herein, the term "FGF receptor" refers to receptors which are able to bind basic FGF and transport it into the cell. Included among these are the receptors described in Imamura, supra and Moscatelli, supra. As used herein, the term "polypeptide reactive with the FGF receptor" refers to any polypeptide which is capable of binding an FGF receptor and of being transported into the cell thereby.

Basic FGF is commercially available, for example, from Amgen (Thousand Oaks, Calif.). Basic FGF can be obtained from a variety of tissue types of mammals. For example, methods of purifying basic FGF using reverse-phase high performance liquid chromatography (RP-HPLC), heparin-Sepharose affinity chromatography and cation exchange HPLC and RP-HPLC are described in U.S. Pat. No. 4,785,079, as well as Gospodarowicz, Proc. Natl. Acad. Sci. 81:6963–6967 (1984) and Gospodarowicz, Meth. Enzym. 147:106–119 (1987), which are incorporated herein by reference. In addition, basic FGF can be synthesized, as by chemical or recombinant methods. Expression of a recombinant protein in yeast and E. coli is described in Barr, et al., J. Biol. Chem. 263:16471–16478 (1988), which is incorporated herein by reference.

The FGF-cytotoxic agent conjugate can be purified on a column containing immobilized heparin. Appropriate columns include heparin-Sepharose and heparin-agarose. The bound conjugate can be eluted with a gradient salt, such as NaCl and is eluted between 1 and 3M.

According to one aspect of the invention, basic FGF is conjugated to a cytotoxic agent so as to target the cytotoxic agent specifically to cells which exhibit FGF receptors. As used herein, the term cytotoxic agent refers to a molecule capable of inhibiting cell function. The term includes agents which are only toxic when transported into the cell and also those whose toxic effect is mediated at the cell surface. A variety of cytotoxic agents can be used including those which inhibit protein synthesis. In one aspect of the invention, FGF is combined with a ribosome-inactivating protein (RIP) such as, for example, saporin-6 (SAP) or other SAP derivatives. SAP is a potent RIP which is isolated from the seeds of the plant *Saponaria officinalis* (See Stirpe, et al., Biochem J. 216:617–625 (1983)). Other appropriate cytotoxic agents include, but are not limited to, ricin, ricin A chain, gelonin, diphtheria toxin, diphtheria toxin A chain and Pseudomonas exotoxin. In another aspect of the invention, the cytotoxic agent is a drug. Examples of such drugs are anthracyclines such as the daunomycins (including daunorubicin and doxorubicin) and methotrexate and its analogs. Others are known to those skilled in the art.

FGF can be conjugated to a protein cytotoxic agent by means known to those skilled in the art, such as through derivitization with a reactive sulfhydryl containing moiety such as SPDP, or via a cross linking agent such as glutaraldehyde or carbodiimide. In one embodiment, the cytotoxic agent is derivatized with a reactive sulfhydryl containing agent, such as N-succinimidyl-3(2-pyridyldithio)propionate. FGF is then added to and mixed with the derivatized cytotoxic agent. The FGF conjugate can be separated from the unreacted products on a column. Alternatively, FGF can be conjugated to a drug, such as 14 bromo doxorubicin through the sugar moiety, as by the cis-aconitate method (Shen and Riser, BBRC 102:1048 (1981), which is incorporated herein by reference).

Alternatively, chimeric FGF-conjugates can be prepared by recombinant methods. Such methods as applied to conjugates of IL-2 or TGFα are provided in Chaudhary et al., Proc. Natl. Acad. Sci. USA 84:4538–4542 (1987) and Lorberman-Galski et al., Proc. Natl. Acad Sci. USA 85:1922–1926 (1988), which are incorporated herein by reference. See also, Maniatis, et al., Molecular Cloning: A Laboratory Manual, Cold Spring Harbor Laboratory (1982), which is incorporated herein by reference.

A conjugate containing FGF and a cytotoxic agent is useful in treating a variety of FGF-mediated pathophysiological conditions. As used herein, the term "FGF-mediated pathophysiological condition" refers to a deleterious condition characterized by or caused by proliferation of cells which are sensitive to basic FGF mitogenic stimulation. Basic FGF-mediated pathophysiological conditions include, but are not limited to, tumors, atherosclerosis, rheumatoid arthritis, Dupuytren's Contracture and certain complications of diabetes such as proliferative retinopathy.

Figure 5:
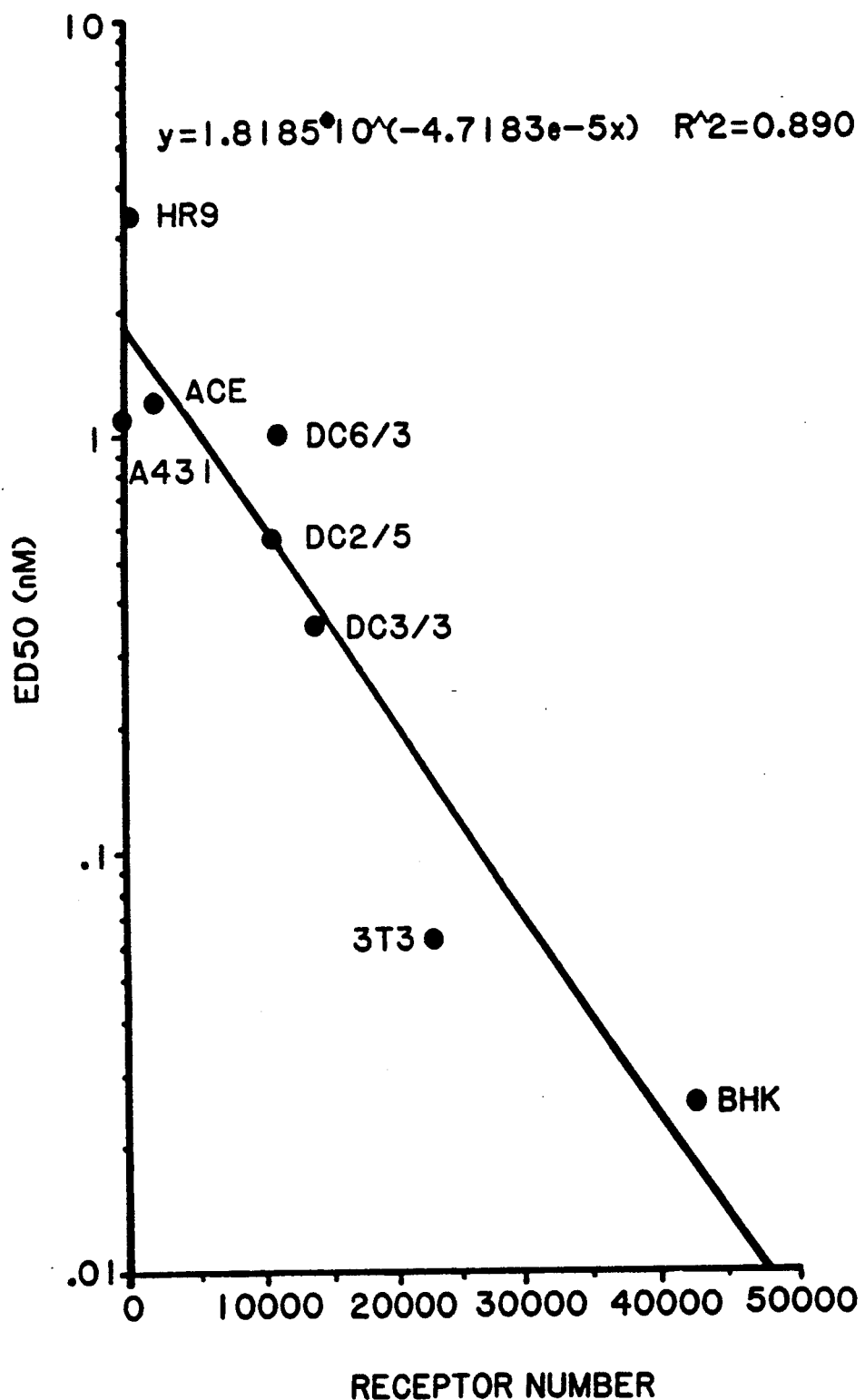
FIG. 5 shows the relationship between toxicity of basic FGF-SAP and FGF receptor number, determined for each cell line after 48 or 72 hours exposure to basic FGF-SAP. Cell numbers were determined and the concentration that reduced the number of cells by 50% was plotted against receptor number for that cell line. Receptor number was determined by the method of Moscatelli et al., supra.

FGF-cytotoxic agent conjugates can be used to target the cytotoxic agent to cells expressing FGF receptors in order to cause cell death. Surprisingly, there is a direct relationship between the number of FGF receptors per cell and the dose at which 50% of the cells are killed (the $ED_{50}$), as is shown in FIG. 5. Moreover, for cells with extremely high receptor numbers, for example, BHK cells, the $ED_{50}$ is identical to the affinity constant of basic FGF for its receptor (both are about 25 pM for BHK cells). This unexpected result indicates that the presence of the cytotoxic agent, even such a large molecule as SAP, does not reduce basic FGF activity. Moreover, these results indicate that these cell that are expressing a large number of basic FGF receptors are particularly sensitive to the conjugate.

In order to treat FGF-mediated pathophysiological conditions, a therapeutically effective amount of FGF-cytotoxic agent conjugate is administered to a mammal in a physiologically acceptable excipient. Examples of physiologically acceptable excipient include PBS and saline.

The following examples are intended to illustrate but not limit the invention.

EXAMPLE I

Conjugation of FGF with Saporin

Recombinant basic FGF corresponding to the sequence of 154 amino acids (Abraham et al., Quant. Biol. 51:657-668 (1986), which is incorporated herein by reference, was obtained from Farmitalia Carlo Erba. Saporin-6 was purified according to the method of Stirpe, et al., supra, as modified by Lappi, et al., Biochem. Biophys. Res. Comm. 129:934-942 (1985), which is incorporated herein by reference. Briefly, seeds of *Saponaria officinalis* were extracted by grinding in 0.14M NaCl in 5 mM sodium phosphate buffer, pH 7.2 (8 ml/g). After overnight stirring at 4° C., extracts were strained through cheese-cloth and were centrifuged at 28,000 g for 30 minutes. The supernatant was separated from the sediment and from floating fat, and is referred to as "crude extract."

Crude extracts were dialyzed against 5 mM sodium phosphate buffer, pH 6.5 centrifuged at 28000 g for 30 minutes and applied to a CM cellulose column (CM 52; Whatman, Maidstone, Kent, U.K.), which after washing, was eluted with a 0–0.3M NaCl gradient in the same buffer. This material was then dialyzed against water and chromatographed on an FPLC Mono S column (Pharmacia, Uppsala, Sweden) equilibrated with 50 mM sodium borate pH 9.5, 0.156M sodium chloride. The protein was eluted with a 20 minute gradient from 0.156M to 0.186M sodium chloride. The resultant peak material was then extensively dialyzed against Milli-Q water (Millipore, Bedford, Mass.). A portion of the dried material was weighed and dissolved in water at a concentration of 1 mg/ml. An ultraviolet spectrum was recorded giving a 1% extinction coefficient of 6.4 at 277 nm, the absorbance maximum. At 280 nm the $E_{280}$ was 6.0. Protein assay using the Lowry method (Lowry, et al., J. Biol. Chem. 193:265-275 (1951) using BSA as a standard gave a result of 1.07 mg/ml.

SAP was derivatized with N-succinimdyl-3(2-pyridyldithio)propionate (SPDP; Pharmacia Fine Chemicals, Piscataway, N.J.) according to the manufacturer's instructions. Briefly, SAP was dissolved in (2.7 mg/mL) in sodium phosphate buffer (0.1M, pH 7.5) containing NaCl (0.1M). A 1.25 molar excess of SPDP, dissolved ethanol, was added by drop while stirring, and allowed to react for 30 minutes at 23° C. with occasional stirring. Excess reagent and low molecular weight reaction products were removed by gel filtration. basic FGF (2 mg/ml) was added to and mixed with the derivatized saporin (6 mg/ml in 0.1M sodium phosphate, 0.1M sodium chloride, pH 7.5) for two hours at room temperature. The reaction was terminated by the addition of 35 μL of 0.1M iodoacetamide. After an additional 30 minutes, the reaction mixture was diluted to 30 ml and loaded onto a heparin-Sepharose (Pharmacia) column (0.5×5.5 cm). The bound proteins were eluted with a step gradient of 0.6M, 1M and 2M NaCl in 10 mM TRIS, pH 7.4. The material eluting between 1M and 2M was pooled. Final purification of the conjugate was achieved after the pool was dialyzed against water and chromatographed on a Mono S 5/5 NaCl cation exchange column (Pharmacia) (buffer A: 50mM sodium borate, pH 8.0, buffer B:0.5M NaCl in buffer A). Fractions containing the conjugate were detected by silver staining after PhastGel (Pharmacia) electrophoresis and appropriate fractions were pooled for analysis.

Synthesis of the conjugate was assessed by gel electrophoresis and allowed to proceed until no detectable basic FGF remained in the reaction mixture. Chromatography on heparin-Sepharose (FIG. 1) and subsequent electrophoretic analysis of each of the peak fractions showed that, while SAP does not bind to heparin-Sepharose, the conjugate does. Only small amounts of the conjugate were released during the 1.0M NaCl wash. The major product eluted with the 2M wash and contained equimolar amounts of SAP and basic FGF (Mr ~40,000). However, there was also a portion of the conjugate that has an estimated Mr>68,000 presumably as a result of the conjugation of two molecules of basic FGF per molecule of saporin.

Unambiguous identification of the SAP-basic FGF conjugate was accomplished using sequence specific antisera raised in rabbits. The immunogen used was a fragment of basic FGF comprising amino acids 1 through 24, chemically synthesized using a 990 Peptide Synthesizer (Beckman Instruments, Brea, Calif.). Western blot analysis showed that all molecular weight forms of the conjugate contained both basic FGF and SAP. The antiserum recognizes the midportion of the peptide and cross-reacts on equimolar basis with purified bovine and recombinant human basic FGF.

Samples in a sodium dodecyl sulfate-containing polyacrylamide gel, after electrophoresis, were electroblotted onto nitrocellulose membranes, and allowed to air dry. The membrane was covered with TRIS buffered saline (TBS) and agitated for 10 minutes. The solution was aspirated and discarded. The membrane was covered with 5% nonfat milk (NFM) in TBS and agitated for 10 minutes. The solution was aspirated and discarded. Primary antibody, either anti-SAP or anti-basic FGF anti-serum, at a concentration of 1/1000 in NFM/TBS was added and agitated overnight. The solution was aspirated and discarded. The membrane was covered with TBS, agitated for 10 minutes and the solution aspirated and discarded. The membrane was covered with 0.05% NP40/TBS and shaken 1 minute; the solution was aspirated and discarded. The final TBS and NP40/TBS washes were replated twice. Horseradish peroxidase labelled anti-IgG at a dilution of 1/2000 in NFM/TBS was added and the membrane agitated for 2 hours. The TBS and NP40/TBS wash steps were repeated. The membrane was placed in a solution (freshly mixed) 60 mg 4-chloro-1-naphthol in 20 mL methanol and 100 mL double distilled water and 10 µL 30% $H_2O$ and the solution added to the membrane and allowed to develop. The solution was aspirated and discarded and the reaction stopped by rinsing with water. The membrane was allowed to dry.

EXAMPLE II

. Activity of the FGF/SAP Conjugate

The capacity of the conjugate to recognize the basic FGF receptor was examined in BHK cells using the procedure described by Moscatelli, et al., J. Cell Physiol. 131:123–130 (1987), which is incorporated herein by reference. Briefly, cells were grown to subconfluence and incubated in 300 µL buffer containing F-12 14 mM $NaHCO_3$, 25 mM HEPES and 0.2% gelatin at 4° C. for two hours with 10 µL radioiodinated basic FGF in the presence of various concentrations of basic FGF or the conjugate. The cells were then washed three times with 0.5 mL phosphate buffered saline (PBS), and twice with 2M NaCl in PBS. Binding to the high affinity receptor was determined by counting the membrane fraction that was solubilized 0.5% Triton X-100 in PBS (pH 8.1).

The protein synthesis inhibition activity of the SAP protein was compared to the protein synthesis inhibition activity of the basic FGF-SAP conjugate in in vitro assays of protein synthesis as described in Siehn et al., Blood 72:756–765 (1988), which is incorporated herein by reference. The cytotoxic activity of the conjugate was tested on baby hamster kidney fibroblasts (ATCC Accession No. CRL 6281). BHK cells were plated in 24 well plates at a concentration of 5000 cells/ml and incubated overnight at 37° C., 5% $CO_2$. The following morning HEPES-buffered DMEM and F-12 media (1:1) plus 5% FCS was aspirated from the wells and replaced with media alone or with media containing the conjugate, basic FGF or saporin. Two days later, the cells were washed twice, trypsinized and cell number determined with a Coulter Particle Counter (Coulter Electronics, Hialeah, Fla.).

Figure 2B:
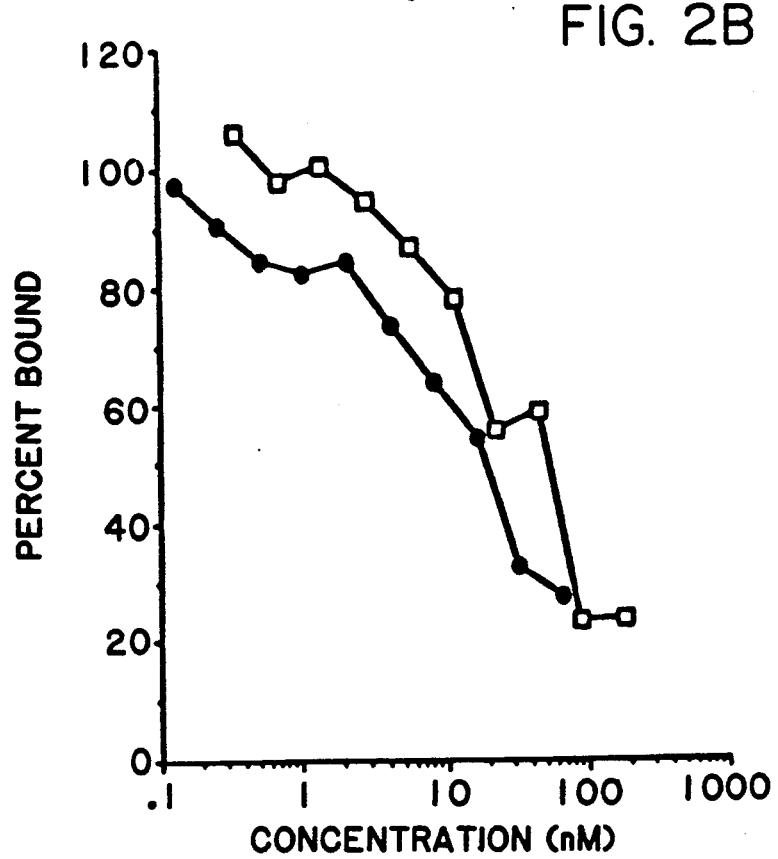
Figure 3:
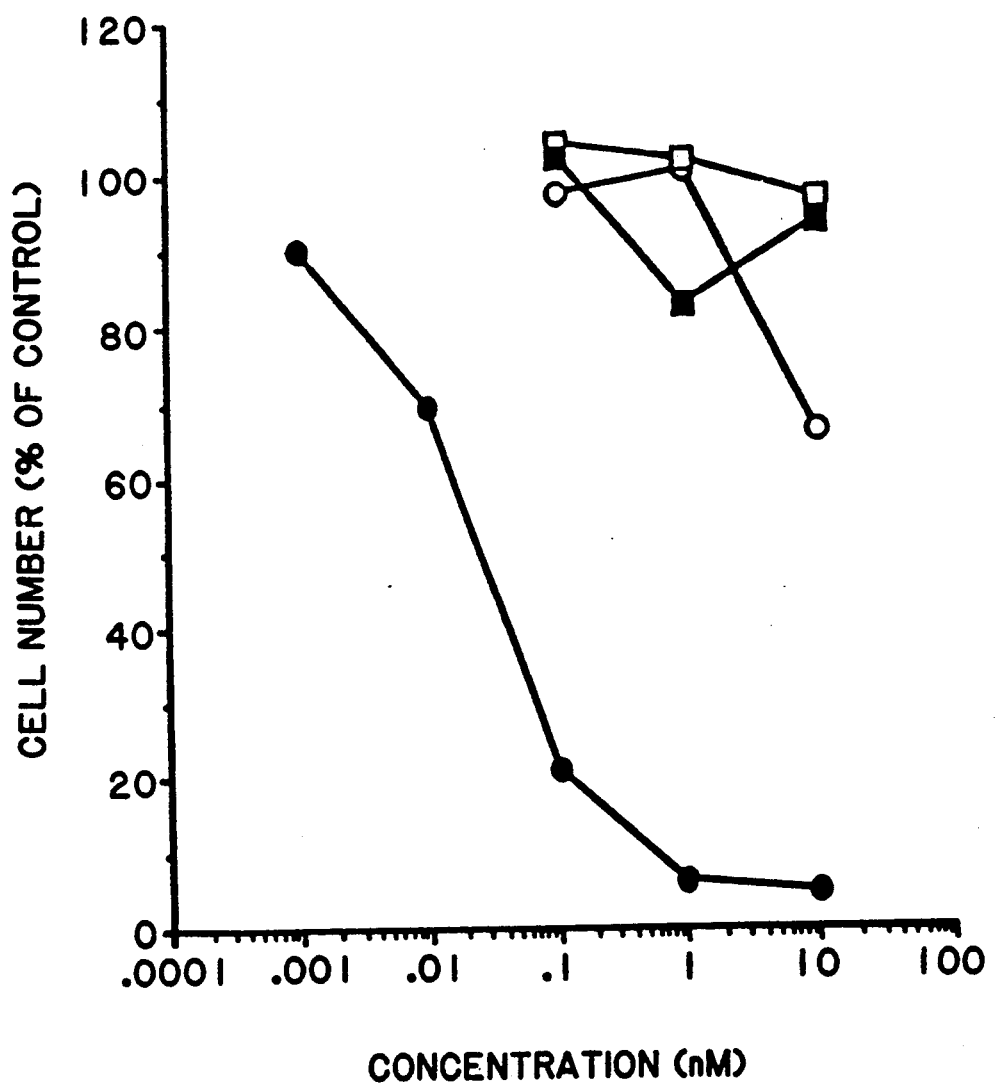
FIG. 3 shows the effect of basic FGF/SAP on BHK cell proliferation. Cell counts were normalized to media controls (190,000±15,000). Cell number with $10^{-8}$M of the mitotoxin was 9,527±980. N=3 in all instances. (basic FGF-SAP ●, SAP ■, basic FGF □, basic FGF+SAP ○).
Figure 4:
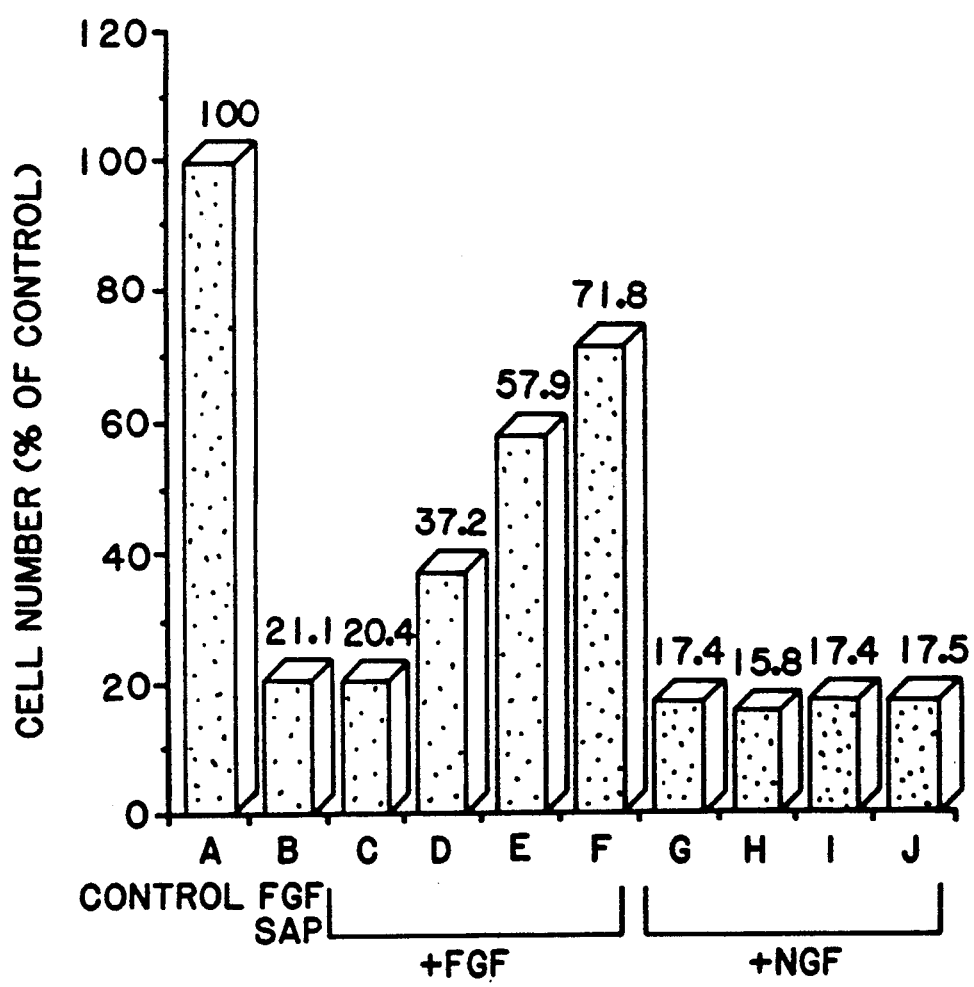
FIG. 4 shows the effect of exogenous basic FGF and NGF on cytotoxicity. Basic FGF-SAP was used at a concentration of $10^{-10}$M basic FGF-SAP and C: preincubation with equimolar free basic FGF, D: 10-fold excess of free basic FGF, E: 100-fold excess of basic FGF, F: 1000-fold excess of basic FGF; G: equimolar incubation with equimolar free NGF, H: 10-fold molar excess, I: 100-fold molar excess, J: 1000-fold molar excess.

As shown in FIG. 2A, the conjugate retains saporin activity when tested in an in vitro protein synthesis inhibition assay. The conjugate, as expected, is slightly less active (about two-fold) than free SAP. This is consistent with the low level of derivatization of SAP prior to the conjugation (0.8 moles SPDP/mole) and with probable steric hindrance due to the presence of bound basic FGF. In contrast, the results obtained in the radioreceptor assays for basic FGF (FIG. 2B) showed that the basic FGF-SAP is equipotent to, if not slightly more active than, basic FGF in the binding assay. Thus, it appears that the commitment of free sulfhydryl groups in basic FGF to bridging with SAP does not interfere with its capacity to recognize its receptor. If anything, this reaction may be stabilizing basic FGF.

basic FGF/SAP is a potent cytotoxic factor for BHK cells (FIG. 3). SAP has no toxic effect on these cells even at the highest dose tested ($10^{-8}$M) and a basic FGF alone has a slight inhibitory effect on proliferation. A mixture of basic FGF and SAP had a slight toxicity but only at the highest concentration tested. The $ID_{50}$ (25 pM) for the cytotoxic agent compares well with the potency of basic FGF (15 pM) in proliferation assays. Specificity of the cytotoxic agent was examined in competition experiments in an effort to establish that the mitotoxic activity of the conjugate is receptor specific. BHK cells were preincubated for one hour with various levels of basic FGF or nerve growth factor (NGF) prior to treatment of the cells with the cytotoxic agent. As shown in FIG. 4, there is a dose-related inhibition of the cytotoxic activity in the presence of increasing amounts of basic FGF. In contrast, a thousandfold excess of NGF has no effect.

EXAMPLE III

Inhibition of Angiogenesis in Rabbit Cornea

Elvax (ethylene-vinyl acetate copolymer resin, Dupont, Wilmington, Del.) pellets were produced in the following manner. About 60 mg of washed and dried Elvax was dissolved in 500 µL of methylene chloride. This was added to 50 µg of dried basic FGF. 5 µL drops were dropped onto a slide frozen in dry ice. Pellets were left in the freezer overnight and then dried in a desiccator.

New Zealand white rabbits were anaesthetized with Innovar Vet: 1 mL/kg. An incision was made in the cornea of the rabbit eye and a pocket was opened with a spatula or forceps. One pellet was inserted in the pocket. Pellets were inserted in both eyes. The eye was washed with saline and 1 ml of gentamicin was injected intramuscularly. The rabbit was left for five days and angiogenesis was observed. After five days, each left eye was treated with 20 µL of 100 ng basic FGF-SAP prepared as in Example I in 0.25% BSA. The right eyes were treated with 20 µL of 0.25% BSA alone. The treatment was done twice daily by dropping the solution as eye drops onto the cornea of the rabbit. The person treating the animals was unaware of the identity of the samples. After 10 days, the animals were evaluated for angiogenesis of the cornea by microscopic analysis by an evaluator who did not know the treatment regimen. Angiogenesis was judged with + + + as being maximal angiogenesis and − as being no angiogenesis.

The results are provided in Table I. As can be seen, angiogenesis in corneas treated with basic FGF-SAP was markedly reduced over that of controls.

TABLE I

| ANIMAL | RIGHT EYE | LEFT EYE |
|---|---|---|
| 995 | + | − |
| 997 | + + + | + |
| 998 | + + + | + |
| 999 | + + | − |

EXAMPLE IV

Effect of FGF-SAP in Dupuytren's Cell

Cells obtained from surgical removal of tissue from the hand of adult patients diagnosed as having Dupuytren's Contracture, a malady effecting movement of the hand, were placed in primary culture. These cells have between 10,000 and 15,000 basic FGF receptors per cell.

Figure 6:
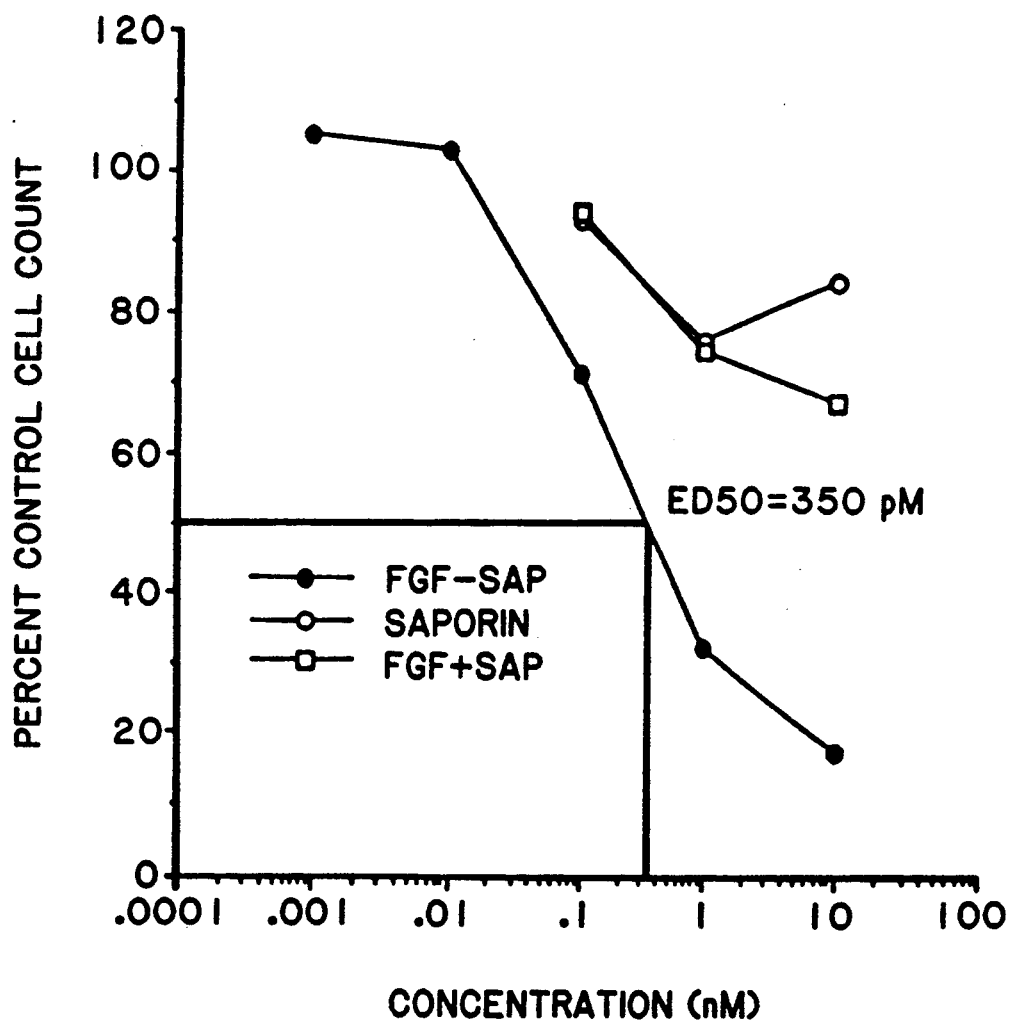
FIG. 6 shows the effect of basic FGF-SAP on Dupuytren's Cells as described in Example IV.

The cells were grown overnight in a 24 well tissue culture dish at a concentration of 10,000 cells per well in HEPES buffered DMEM with 10% FCS. The next morning the media was removed and replaced with media containing concentrations of basic FGF-SAP conjugate ranging from $10^{-8}$ to $10^{-12}$ molar. Controls included wells treated with media only, wells treated with similar concentrations of basic FGF alone, saporin alone, and basic FGF and saporin together but not conjugated. The cells were returned to the incubator for 72 hours. At the end of this incubation the cells were washed, removed with trypsin and counted on a Coulter cell counter. The number of cells in the media controls was compared with the number of cells in the treated wells (as described above). The results of these cell killing assays are shown in FIG. 6. As can be seen, Dupuytren's cells are sensitive to basic FGF-SAP. Similar results were obtained with three other cell samples.

Although the invention has been described with reference to the presently-preferred embodiments, it should be understood that various modifications can be made without departing from the spirit of the invention. Accordingly, the invention is limited only by the following claims.

We claim:

1. A conjugate comprising saporin and basic FGF which is reactive with an FGF receptor.

2. A pharmaceutical composition comprising a conjugate of basic FGF with saporin, and a physiologically acceptable excipient.

* * * * *

UNITED STATES PATENT AND TRADEMARK OFFICE
CERTIFICATE OF CORRECTION

PATENT NO. : 5,191,067
DATED : March 2, 1993
INVENTOR(S) : Lappi, et al.

It is certified that error appears in the above-identified patent and that said Letters Patent is hereby corrected as shown below: Title page:
Item [56]

TITLE PAGE: Under "Other Publications", line 7, change "vol. 50" to --vol.80--; line 12, change "EGF-Saporin" to --FGF-Saporin--.

Column 1, line 5, insert: --This invention was made with Government support under Grant AM-18811 awarded by the National Institutes of Health (DHHS). The Government has certain rights in this invention.--
Column 2, line 37, after "SAP", delete the comma (,); Column 2, line 55, after "FGF", (second occurrence), change the semicolon (;) to a comma (,); Column 3, line 21, change "hst. int-2" to --hst, int-2--. Column 5, line 26, change "cell" to --cells--. Column 6, line 17, change "basic" to --Basic--. Column 8, line 3, change "basic" to --Basic--.

Signed and Sealed this

Fifteenth Day of March, 1994

Attest:

BRUCE LEHMAN

Attesting Officer             Commissioner of Patents and Trademarks